Figure 1:
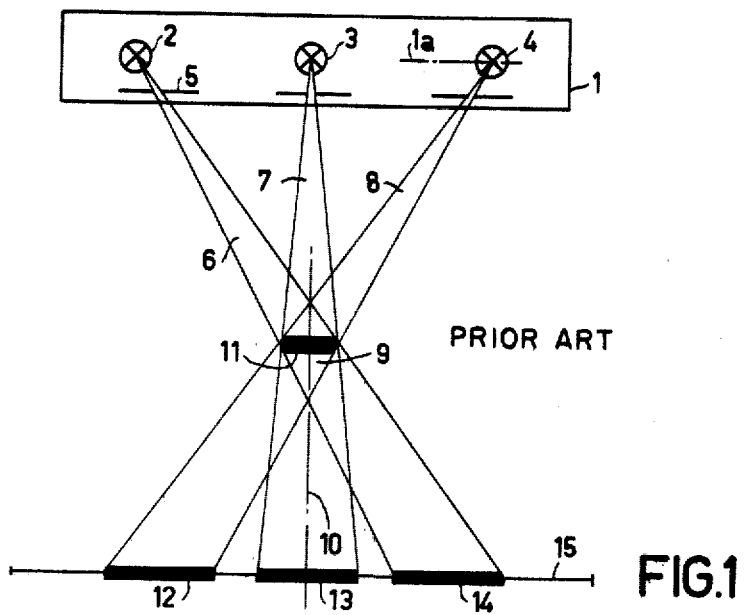

United States Patent [19]

Dallas

[11] 4,305,095

[45] Dec. 8, 1981

[54] METHOD OF MAKING PLANIGRAMS OF A THREE-DIMENSIONAL OBJECT

[75] Inventor: William J. Dallas, Hamburg, Fed. Rep. of Germany

[73] Assignee: U.S. Philips Corporation, New York, N.Y.

[21] Appl. No.: 132,919

[22] Filed: Mar. 24, 1980

[30] Foreign Application Priority Data

Mar. 23, 1979 [DE] Fed. Rep. of Germany ....... 2911375

[51] Int. Cl.$^3$ ............................................. H04N 9/54
[52] U.S. Cl. ......................................... 358/88; 358/3; 358/6; 352/45; 350/174
[58] Field of Search ...................... 358/88, 89, 2, 3, 4, 358/5, 6, 7, 127; 352/86, 45, 57; 350/316, 317, 130, 174

[56] References Cited

U.S. PATENT DOCUMENTS

| | | | |
|---|---|---|---|
| 3,493,290 | 2/1970 | Traub | 358/89 |
| 3,943,279 | 3/1976 | Austefjord | 358/88 |
| 4,190,856 | 2/1980 | Ricks | 358/88 |

*Primary Examiner*—Robert L. Richardson
*Assistant Examiner*—Edward L. Coles
*Attorney, Agent, or Firm*—Thomas A. Briody; Robert T. Mayer; Jack E. Haken

[57] ABSTRACT

In order to make planigrams of a three-dimensional object, the object is irradiated from different directions in order to form a superposition image which consists of separate perspective images. Multiple imaging of the superposition image is realized by means of an imaging matrix, the individual perspective images being superposed in a zone which is situated behind the imaging matrix and in which, for example, a ground glass plate can be arbitrarily positioned for the imaging of layer images. During the superposition of the individual perspective images by means of the associated imaging elements of the imaging matrix, however, artefact images are caused by the transmission of perspective images by inappropriate imaging elements. These artefact images are suppressed in that on each artefact image a correction perspective image, derived from a perspective image, is superposed via an additional imaging element in order to compensate for the artefact image.

11 Claims, 24 Drawing Figures

FIG.4 i

FIG.5

METHOD OF MAKING PLANIGRAMS OF A THREE-DIMENSIONAL OBJECT

The invention relates to a method of and a device for making planigrams of a three-dimensional object which is irradiated by a large number of radiation sources which are arranged in one plane in order to form a superposition image which is composed of separate primary perspective images, said superposition image subsequently being imaged by means of an optical imaging matrix whose imaging elements are distributed in accordance with the distribution of the radiation sources, the imaging elements being positioned with respect to the primary perspective images so that central rays of radiation beams which transmit the primary perspective images via the associated imaging elements intersect behind the imaging matrix in a point situated on an optical axis which is directed perpendicularly to the imaging matrix, in the superposition zone of the radiation beams there being formed a real image of the object wherefrom planigrams can be formed by means of a record carrier.

A method of this kind is described in German Patent Application No. P 27 46 035. According to this method, an object is simultaneously irradiated from different directions by means of a source matrix which consists of a plurality of radiation sources which are arranged in one plane, separate perspective images forming a superposition image on, for example, a film plate. During a subsequent decoding step, reconstruction takes place by means of the superposition image in order to form separate planigrams of the three-dimensional object.

The decoding can be illustrated as follows: in order to make an image of a given, arbitrary flat slice of the object, the superposition image is shifted and summed a number of times which equals the number of sources used for the irradiation of the object. The superposition image is then shifted so that all associated primary perspective images are made to register in order to obtain a planigram (German Offenlegungsschrift No. 24 31 700).

A decoding step of this kind can be performed, for example, by means of an imaging matrix which is arranged in front of a superposition image which is illuminated from the rear, the distribution of the imaging elements of the imaging matrix corresponding to the distribution of the separate radiation sources of the source matrix. Each separate primary perspective image is then transmitted by an associated imaging element so that the central rays of the radiation beams which transmit the primary perspective images via the associated imaging elements intersect behind the imaging matrix in a point on an optical axis which extends perpendicularly through the imaging matrix, in the superposition zone of the radiation beams there being formed a real image of the object wherefrom layer images can be derived by means of, for example, a ground glass plate. The central rays are to be understood to mean the rays which extend through the centres of the primary perspective images as well as through the centres of the imaging elements. However, primary perspective images are not only transmitted by means of the associated imaging elements, but also at the same time by inappropriate imaging elements, so that these primary perspective images are imaged as artefact images together with the desired layer image, in an image plane in the superposition zone.

Therefore, the invention has for its object to provide a method which enables the formation of arbitrary planigrams of a three-dimensional object which are artefact-poor (that is, which have few artefacts), at least at their center.

This object is achieved in accordance with the invention in that, in order to obtain planigrams which are artefact-poor at least in their centre, artefact images which are caused by transmission of primary perspective images by inappropriate imaging elements are suppressed by means of additional elements in that on each artefact image a correction perspective image derived from a primary perspective image is superposed, via an additional imaging element so that the artefact image is compensated for.

The correction perspective images derived from the primary perspective images are superposed on the artefact images by means of additional imaging elements which are included in the imaging matrix and which are arranged each time in the beam path between an artefact image to be compensated for and a suitable primary perspective image. Obviously, these image-transmitting imaging elements also transmit correction perspective images to locations where there are no artefact images to be compensated for. At these areas new artefact images are formed which are compensated for by means of imaging elements, to be included in the imaging matrix, and primary perspective images which serve as correction perspective images. The magnitude of the area in which the artefact images in the reconstructed layer image can be compensated for can be chosen at random and is dependent only of the magnitude of the imaging matrix or of the structure and the number of imaging elements of the imaging matrix.

In a preferred embodiment in accordance with the invention, lenses are used for the imaging elements and a lens matrix is used as the imaging matrix, a first filter being arranged in the beam path of the lenses used for transmitting the primary perspective images, a second filter which differs from the first filter being arranged in the beam path of the lenses used for transmitting the correction perspective images, the radiation passing through the filters being detected by image pick-up tubes, a first input filter which corresponds to the first filter being arranged in front of the one tube, and a second input filter which corresponds to the second filter being arranged in front of the other tube. The video signals of the image pick-up tubes are subtracted from each other in order to obtain layer images.

The different filters in the relevant beam paths ensure that only a single superposition image consisting of primary perspective images has to be made. The formation of a superposition image consisting of correction perspective images can thus be dispensed with. When the superposition image is irradiated from the rear, for example, by means of white light, two different colour filters can be used, for example, a red filter and a blue filter. The red filters are then arranged, for example, in the beam path of the lenses transmitting the primary perspective images, whilst the blue filters are arranged in the beam path of the lenses which serve to superpose the correction perspective images on the artefact images. The image pick-up tubes, comprising corresponding input filters, each time detect only one colour in order to make corresponding colour images which are electronically subtracted from each other in order to form artefact-free layer images.

Said filters and input filters, however, may also be other filters, for example, polarization filters.

Embodiments in accordance with the invention will be described in detail hereinafter with reference to the accompanying diagrammatic drawing.

Figure 2:
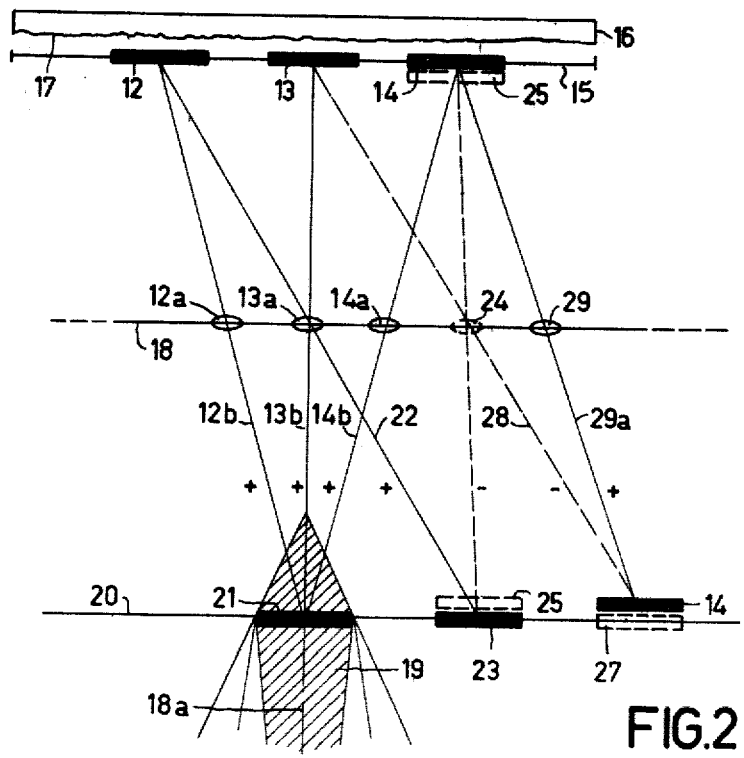
Figure 6:
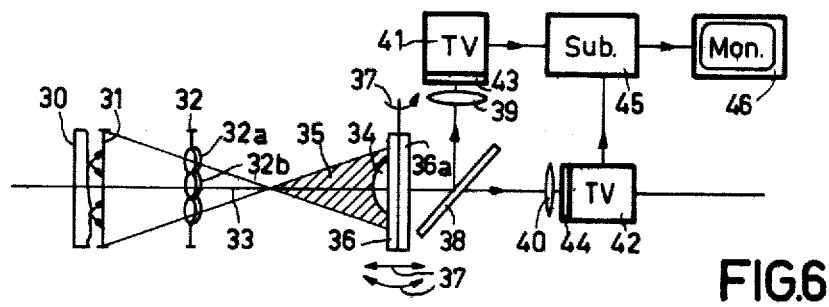
Figure 7:
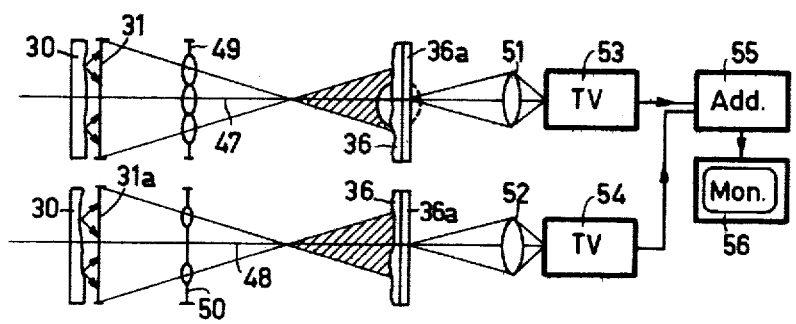
Figure 8:
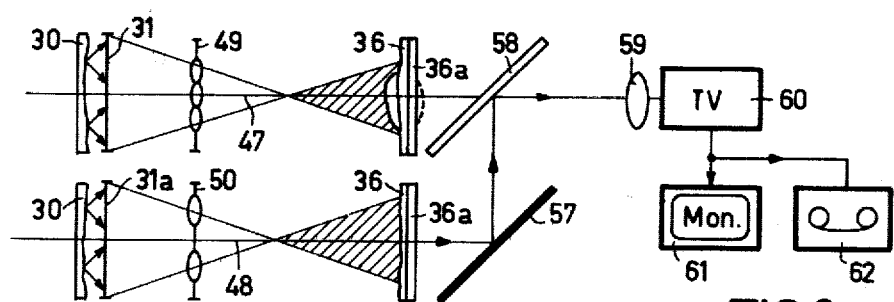
Figure 9:
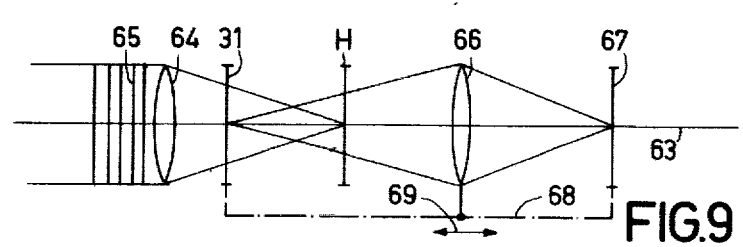
Figure 10:
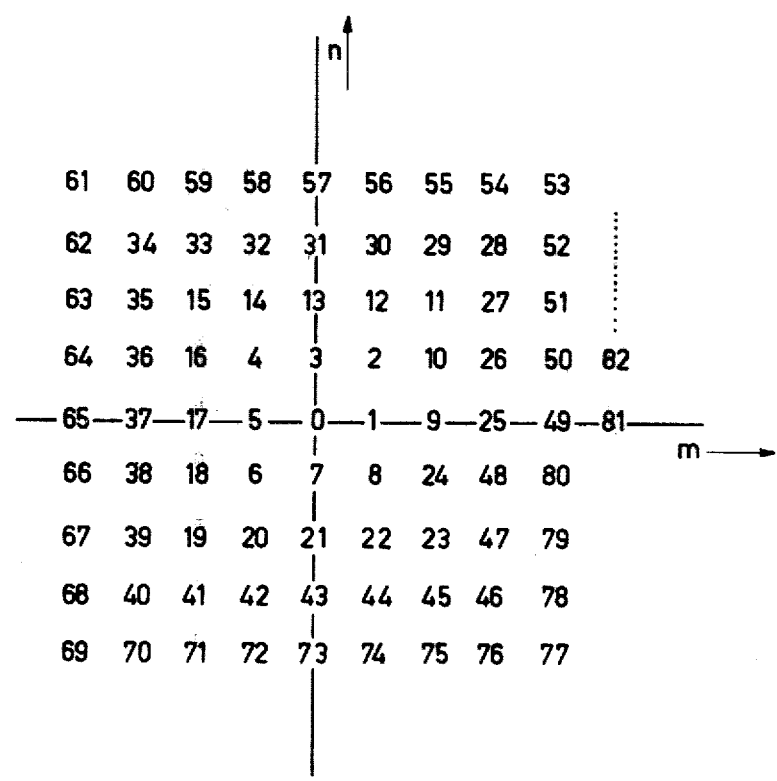

FIG. 1 shows the recording of a superposition image consisting of primary perspective images, FIG. 2 shows the reconstruction of a layer image from the superposition image by means of a lens matrix and the compensation of artefact images, FIGS. 3a–g illustrate a recording code consisting of two points and the step-wise building up of a compensation distribution which is correlated to the recording code, FIGS. 4a–i show a recording code consisting of three points and the step-wise building up of a further compensation distribution which is correlated to the recording code, FIG. 5 shows a three-point recording code which is correlated to a distribution which corresponds to the recording code, FIG. 6 shows a device for making layer images which are artefact-free at least in their centre, FIG. 7 shows a further device for making layer images with separate optical and electronic channels, FIG. 8 shows a device comprising separate optical channels and a common electronic channel, FIG. 9 shows a device for making artefact-free layer images by way of holography, and FIG. 10 shows a table of characteristic numbers.

The foregoing description, and also the following description, is given with reference to X-ray super-position images. However, images of particle radiation normal optical and electronic images can also be processed according to this method without restriction. Artificial images calculated by a computer can also be processed by the method in accordance with the invention.

FIGS. 1 and 2 serve to illustrate the principle of the method in accordance with the invention. FIG. 1 shows a multiple radiation source 1 which comprises, for example, three separate radiation sources 2, 3 and 4 which are arranged in a plane 1a. A so-termed point-image function indicates the positions of the separate radiation sources in the plane 1a.

The separate radiation sources 2, 3 and 4, which can be simultaneously flashed, emit X-ray beams 6, 7, 8 which are stopped by apertures 5 and which intersect on an optical axis 10 (which extends perpendicular to the plane of the radiation sources) in order to irradiate an object 11 to be examined. The object 11 is thus recorded in a coded manner in that three separate primary perspective images 12, 13, 14 are imaged, for example, on a single film 15.

FIG. 2 shows the decoding step. The separate primary perspective images 12, 13, 14 on the film 15 are irradiated by means of a light box 16, which comprises, for example, a flat ground glass plate 17 at its front, and are imaged by means of a lens matrix 18 so that the central rays 12b, 13b, 14b of the radiation beams transmitting the primary images 12, 13, 14 intersect each other behind the lens matrix 8 in a point on an optical axis 18a which extends perpendicularly through the lens matrix 18. The radiation beams are superposed in a zone 19. The primary perspective images 12, 13, 14 are thus imaged by means of the associated lenses 12a, 13a, 14a. In the superposition zone 19 there may also be arranged a scatter disc 21, or a similar device, which can be arbitrarily positioned in order to make the layer images 21 of the object 11 visible; oblique layers of the object 11 can thus also be reproduced.

An artefact image in the imaging plane 20 is formed because the separate primary perspective images 12, 13, 14, for example, being positive, are also transmitted by the inappropriate lenses. For example, the primary perspective image 12 is also transmitted, via the lens 13a, by way of a beam 22, so that in the imaging plane 20 an artefact image 23 is produced which corresponds to the primary perspective image 12. In order to compensate for this artefact image 23, an additional lens 24 is included in the imaging matrix 18. Via this additional lens 24, a correction perspective image 25 (negative), derived from the primary perspective image 14; is transmitted by way of a beam 26; and is superposed on the artefact image 23, so that they cancel each other. The correction perspective image 25 can be obtained from the primary perspective image 14 or from the total superposition image 15.

The additional lens 24 also transmits further correction perspective images 27 which are situated in the imaging plane 20, for example, via a beam 28, and which are produced in conjunction with the compensation of the artefact image 23 by the correction perspective image 25. This is because the correction perspective image 25 was obtained from the superposition image 15, thus from the primary perspective image 13.

The correction perspective image 27 (for example, a negative image) itself is then compensated for by means of a further lens 29 introduced into the lens matrix 18, so that, via a beam 29a, the primary perspective image 14 (positive) is superposed, via the lens 28, on the correction perspective image 27, so that the two images 14 and 27 cancel each other. Obviously, the primary perspective images and the correction perspective images are not transmitted in succession. For example, during a first step all primary perspective images 12, 13, 14 can be simultaneously transmitted via the lenses 12a, 13a, 14a and 29, whilst the correction perspective images 25 and 27 are transmitted, by way of the beams 26 and 28 during a second step, via the lens 24. Both transmissions can also be simultaneously performed; this will be elaborated hereinafter.

Using the method in accordance with the invention, therefore, within a layer image representing a given object layer the artefact images are compensated for which were produced during the reconstruction by transmission of primary perspective images from the corresponding object layer.

FIGS. 3a–g and 4a–i illustrate how the positions of the lenses 24 and 29 in FIG. 2 are determined.

As has already been stated, the lenses 12a, 13a, 14a, are arranged in the plane 1a in accordance with the distribution of the radiation sources 2, 3 and 4 i.e. distributed in accordance with the point-image functions of the recording geometry (radiation source array) in the lens matrix 18.

Figure 3:
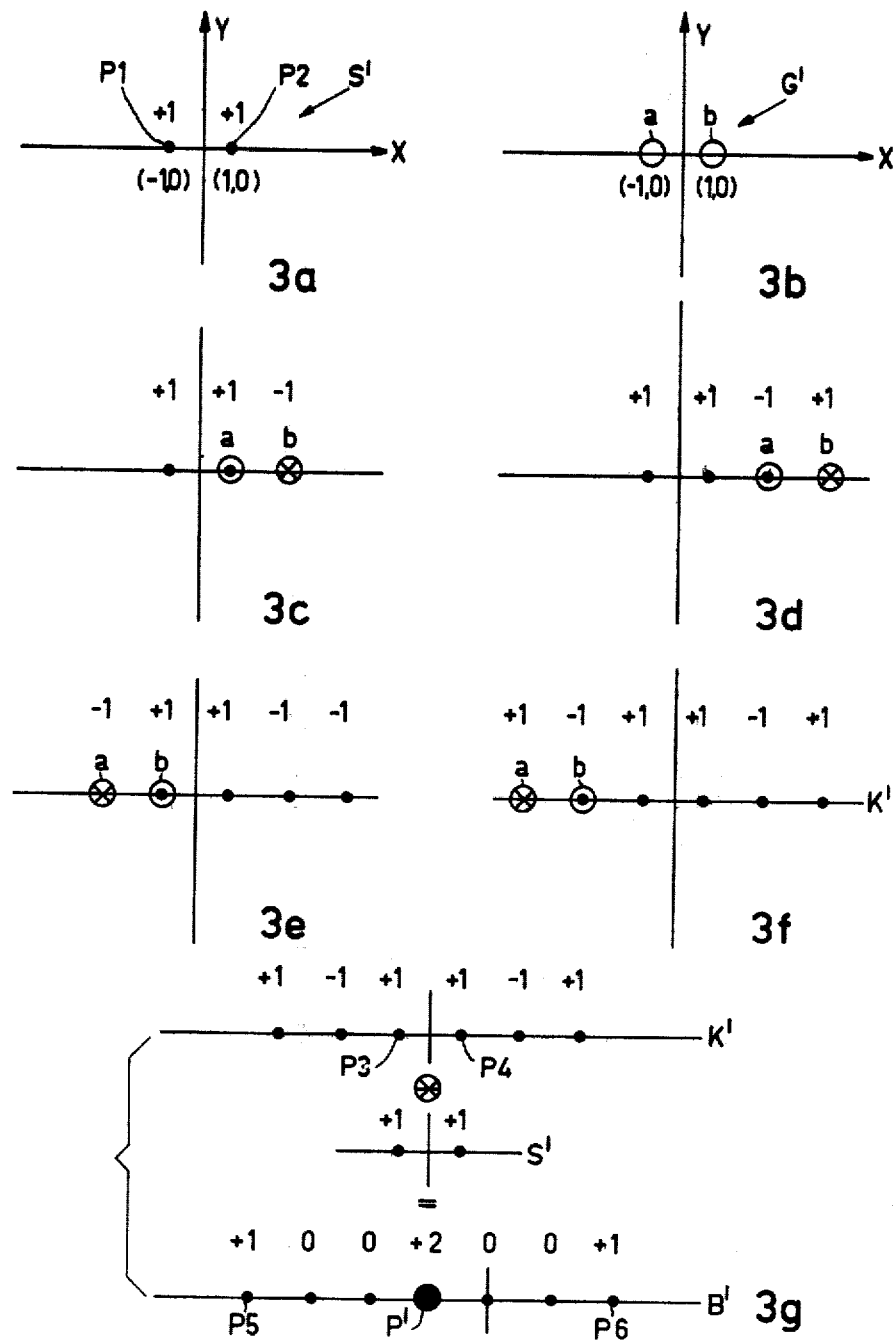

FIG. 3a shows a so-termed recording code S' wherefrom a compensating code K' (FIG. 3f) can be derived which contains the recording code S', the compensating code K' being correlated to the recording code A' in order to obtain layer images which are artefact-poor at least in their centre (FIG. 3g).

To enable a clear illustration of the situation, it is assumed that the object 11 consists only of a point p' (not shown) and that two X-ray sources (not shown) having the same intensity are used for irradiating the object 11. Obviously, the object 11 may alternatively have a shape other than that of a point. It may form part of a human body, for example, a human organ.

The first phase of the method consists in the recording of the object (point) on a separate recording material by means of the two X-ray sources. On the recording material there are produced two points P1 and P2 whose distribution corresponds to the distribution of the X-ray sources. FIG. 3a shows such a distribution of two points P1 and P2 (in a coordinate system X, Y) which have the coordinate (X,Y)=(−1, 0) and (+1, 0) and an amplitude (for example, density) of +1. A point distribution of this kind is referred to hereinafter as the recording code S'.

From this recording code S' there is derived a compensating code K' (FIG. 3f) which in this case consists of a line of points. To this end, a generator G' which is shown in FIG. 3b, is defined which consists of two circles a and b having the coordinates (−1, 0) and (1, 0). When this generator G' is positioned on the recording code S' and is subsequently shifted in the positive or negative X direction until a point of the recording code S' arrives in a circle a or b of the generator G', a new point is determined each time in the free generator circle, the amplitude of the new point is the negative amplitude of the point of the recording code S' which is situated in the other generator circle. Superposition of the two generator circles with both points of the recording code S' is then precluded.

In FIG. 3c, the generator G' has been shifted to the right. In the generator circle b, therefore, a point having the amplitude −1 is situated. In FIG. 3d, the generator has been shifted one step further to the right. The generator circle a then covers a point having the amplitude −1, so that in the generator circle b a point having the amplitude +1 is situated, etc. In FIG. 3e, the generator G' has been shifted in the negative direction. In the circle a of the generator G', now performing a translatory movement, a point having the amplitude −1 is situated, because a point having the amplitude +1 is situated in the generator circle b. Further shifting of the generator to the left produces an additional point having the amplitude +1 in the generator circle a (FIG. 3f). The formation of the compensating code K', shown in FIG. 3f, which still contains the recording code (the two inner points P3 and P4 must be interrupted at this point).

When this compensating code K' is correlated with the recording code S' as shown in FIG. 3g (i.e. the K'⊕S') a quasi-one dimensional image B' is obtained of the point P' having the amplitude 2 and also two secondary points P5 and P6, each having the amplitude +1, which are situated comparatively far from the centre of the image B'. These secondary points represent the artefact images which, however, can be readily pushed to the outside by enlargement of the compensating code K'. The centre of the image B' therefore, is free of artefacts. The operation K'⊕S⊕( =correlation) only means that the compensating code K' is shifted with respect to itself so that each time an inner point P3, P4 is made to register with an other point. Subsequently, all registering points are summed and the image B' is obtained. The number of shifts of the compensating code K', therefore, is determined on the basis of the n points in the recording code S'. In the above example, therefore, n-1 shifts are performed. Alternatively, n shifts can be performed if both inner points P3, P4 of the compensating code K' are shifted over only half the mutual distance with respect to each other, after which they are made to register.

The correlation ⊕ need not be necessarily executed by the shifting of a compensating code K' in the form of a point image. The compensating code K' can alternatively be realized by a one-dimensional row of lenses which are situated at the points of the code K'. Referring to FIG. 2, therefore, the compensating code K' could be realized in the lens matrix 18 and the recording code S' would correspond to the superposition image 15. A further example concerning a three-point recording code S" land the making of a correspondisng compensating code K" will be described with reference to the FIGS. 4a-i.

For the clarity of the description a point-like object P' is again chosen instead of a part of, for example, a human body. This object P' is recorded by means of X-ray sources (not shown) which are situated in one plane at the corners of a right-angled triangle. After the recording of the object P", therefore, a point image is obtained on a single recording material, the points P7, P8 and P9 thereof being situated on the record carrier in accordance with the distribution of the X-ray sources. The points P7, P8 and P9 are situated, for example, at the coordinates (−1, +1), (−1, −1) and (+1, −1) within the coordinate system X, Y and all have the same amplitude +1.

Figure 4:
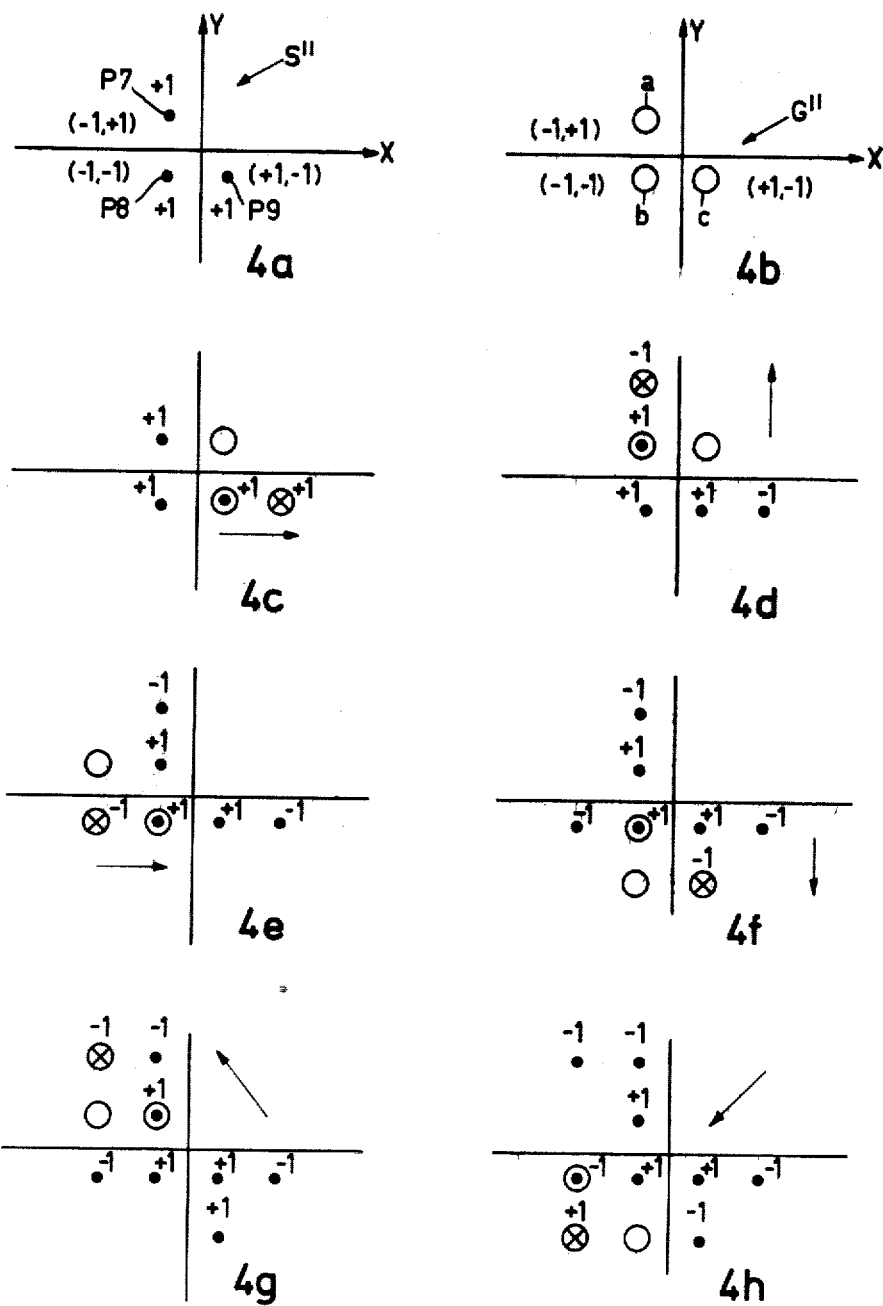
Figures 4I, 5:
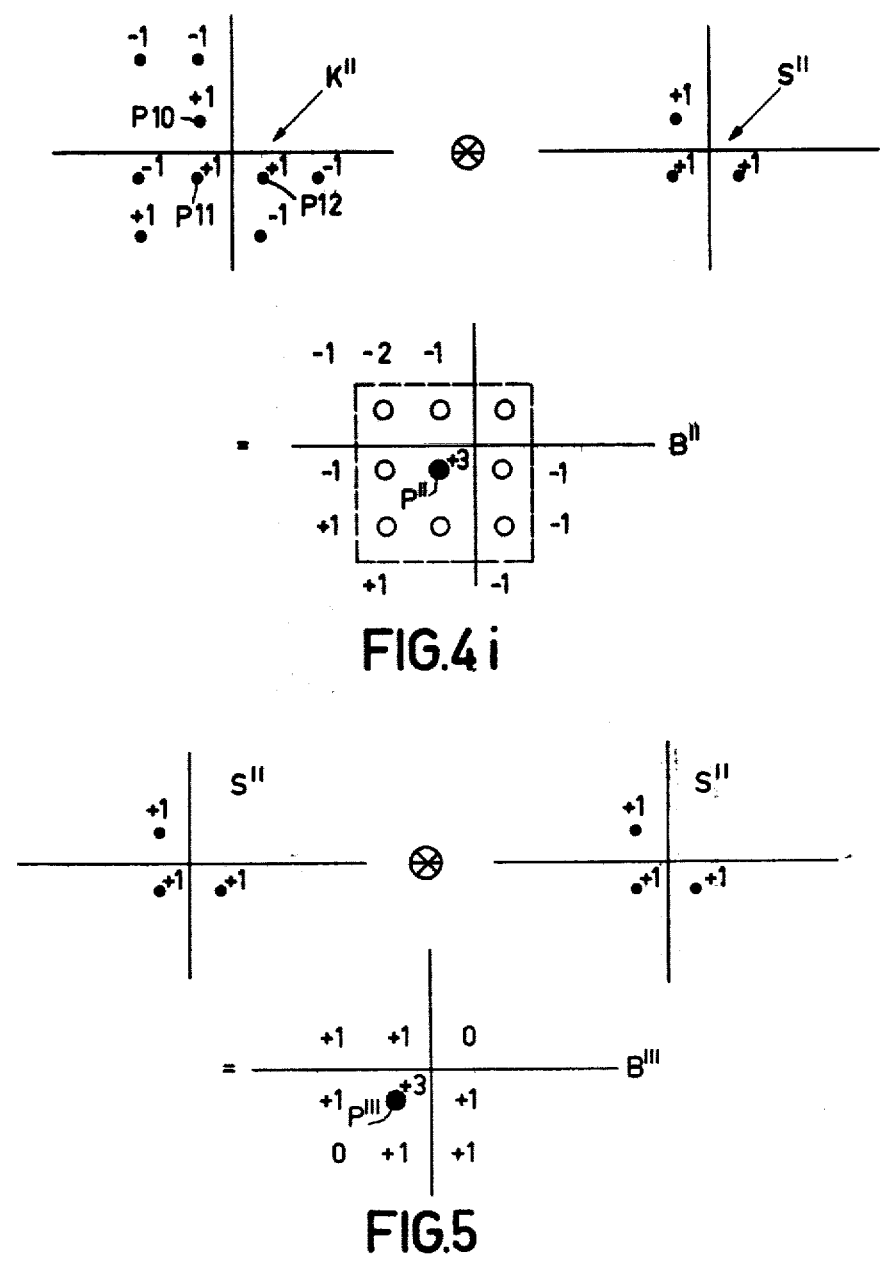

A corresponding generator G" then has generator points a, b and c which are also situated at the coordinates (−1, +1), (−1, −1) and (+1, −1) (FIG. 4b). In order to form a compensating code K", this generator G" is accurately positioned on the recording code S" and is shifted with respect thereto by translatory movements. A simultaneous superposition of the generator points a, b and c on all points P7 to P9 of the recording code S" is again precluded.

The generator circle a, b or c in which each time a point is inserted for the building up of the condensating code K" is determined by the shifting of the generator G" with respect to the recording code S".

I. For shifts of the generator G" to the right (+x), downwards to the right or downwards (−y), the generator circle c is used, II. for shifts in the upwards direction (+y) or upwards to the left, the generator circle a is used, III. for shifts to the left (−x) or downwards to the left, the generator circle b is used, IV. in the case of shifts upwards to the right, the generator G" does not cover points of the recording code S", so that in this case no points which contribute to the formation of a compensating code K" are formed in the first quadrant of the coordinate system.

As is shown in FIG. 4c, the generator G" is shifted in the positive x-direction so that the generator circle b thereof surrounds the point P9 of the recording code S". In this case it is laid down that in the generator circle c a point is inserted having an amplitude which is the negative sum of the amplitudes of the points situated in the other generator circles a and b. The generator circle c thus obtains a point having the amplitude −1.

In FIG. 4d the generator is shifted upwards (+y), so that in the generator circle a a point having the amplitude −1 is inserted, whilst in the generator shifted to the left in FIG. 4e a point having the amplitude −1 is also inserted in the generator circle b. A downwards shift (−y) of the generator as shown in FIG. 4f produces a point having the amplitude −1 in the generator circle c. A further upwards shift to the left in FIG. 4g produces a point having the amplitude −1 in the generator circle a. A downwards shift to the left (FIG. 4b) produces a further point having the amplitude +1 in the generator circle b.

FIG. 4a clearly shows the compensating code K" again. Obviously, this code can be increased as desired by shifting the generator G" approximately counter-clockwise in the described manner in order to find new points for building up a larger compensating code. In order to make layer images B" which are artefact-poor at least in their centre, the compensation code K" thus obtained is correlated to the recording code S". The operation K"⊕S" means that each time the total compensating code K" is shifted so that the points P10 and P12 are positioned on the P11 and are summed. The further points of the compensating code K" registered during this shift are also summed, so that the image B" is formed. This image internally has a point P" having the amplitude +3, whilst around this point P" an artefact-free area is present. The secondary points (artefact images) are situated more or less in the vicinity of the edge of the image and can be shifted arbitrarily further outwards by increasing the compensating code K".

Again it is not necessary to perform the corresponding ⊕ by the shifting of a compensating code K" in the form of a point image. The correlation can be realized instead by means of a lens matrix whose lenses are situated at the points of the compensating code K".

The lenses which are situated at the points of positive amplitude of a compensating code thus transmit the primary perspective images, whilst the lenses which are situated at the points of negative amplitude of the compensating code transmit the correction perspective images which are superposed on the artefact images. Obviously, a compensating code may also comprise points having an amplitude other than 1, for example, +2. The lens to be situated at this point must then be so large that it can transmit a corresponding amount of light for compensation of the artefact images.

FIG. 5 shows an autocorrelation of the recording code S" for the purpose of comparison. The shifting and summing of the individual points (or images) produces a principal point P'" which is surrounded by further points which represent artefact images and which are situated substantially nearer to the centre of the image P'" than the artefact images in the image B" of FIG. 4i.

The arithmetical determination of a compensating code K for a predetermined recording code S will be described in detail hereinafter.

First of all, the following general matrices are defined:

(a) Smn = recording code (S', S")

Kmn = reconstruction code (compensating code K', K"),

Tmn = Kmn − Smn = compensation part of the reconstruct code, $$A_{mn} = \sum_{j=-\infty}^{\infty} \sum_{k=-\infty}^{\infty} S_{m+j, n+k} S^*_{jk} = S \oplus S =$$

autocorrelation of the recording code (1)

$$B_{mn} = \sum_{j=-\infty}^{\infty} \sum_{k=-\infty}^{\infty} S_{m+j, n+k} K^*_{ij} = S \oplus K =$$

crosscorrelation of recording code and reconstruction code (2)

$$C_{mn} = \sum_{j=-\infty}^{\infty} \sum_{k=-\infty}^{\infty} S_{m+j, n+k} T^*_{ij} = S \oplus T =$$

crosscorrelation of the recording code and the compensation part of the reconstruction code (3).

The characteristic numbers m and n are integer numbers (m, n = 0, ±1, ±2, . . . ), while the symbol * each time characterizes conjugated complex quantities.

(b) The codes used (Smn, Kmn, Tmn) are represented as a flat distribution of points, the points of the point distribution being elements of a matrix.

The position of the points within the matrix is determined by the characteristic numbers m, n resulting from the coordinates of the points, divided by the lattice distance of the matrix. The dimensions of the matrix elements determine, for example, the intensity of the points. For the further description, an example is used in the form of a point distribution which represents a recording code Smn and which consists of two points. Both points have the value or the intensity +1, whilst the coordinates thereof are ($x_1 = +0.1$ mm, $y_1 = 0$ mm) and ($x_2 = -0.1$ mm, $y_2 = 0$ mm). These coordinates correspond to the position coordinates of the radiation sources used to irradiate an object. They have only been reduced by the same factor. When a suitable lattice distance is chosen for the matrix, for example, 0.1 mm and if the zero point of the matrix is determined as ($x_0 = 0.$ mm, $y_0 = 0.0$ mm), the two points can be denoted as matrix points $S_{1,0} = 1$ and $S_{-1,0} = 1$. All other elements of the matrix have the value 0.

(c) The centre of the artefact-free reconstruction image is situated in the point m = 0, n = 0. The intensity of this point is given by the matrix element $B_{0, 0}$. All other elements Bmn which are not zero, represent artefacts, i.e Bmn is the extent of an artefact at the lattice point (m, n) (see the FIGS. 3g and 4i).

The aim is to create an artefact-poor area around an artefact-free reconstruction centre by means of a compensation code. A quadratic area having sides of a length $2m_o$ is chosen by way of example. The lattice constants in the x direction and the y direction are the same. All matrix elements Bmn must be zero in this area, that is to say Bmn = 0 for all $|m| < m_o$ or $|n| < m_o$. An exception in this respect is formed by the element $B_{0,0}$ for which $$B_{0,0} \neq 0.$$

(d) The reconstruction code Kmn (compensating code) consists of two parts: the recording code Smn and the compensation part Tmn of the reconstruction code Kmn.

$$K_{mn} = S_{mn} + T_{mn} \quad (4)$$

Therefore, the matrix Bmn also consists of two parts $$B_{mn} = \sum_{j=-\infty}^{\infty} \sum_{k=-\infty}^{\infty} S_{m+j, n+k} S^*_{jk} + \quad (5)$$

$$\sum_{j=-\infty}^{\infty} \sum_{k=-\infty}^{\infty} S_{m+j, n+k} T^*_{jk}$$

$$= A_{mn} + C_{mn} = S \oplus S + S \oplus T \text{ (see equations 1-3).}$$

The matrix Amn contains the position and the extent of the points reconstructed without disturbance, but also the position and the extent of artefacts (for example, see FIG. 5). The matrix Cmn, however, only contains artefacts of reverse sign. When Amn and Cmn are summed, the artefacts in the preselected area disappear. Thus, the aim is for:

$Cmn = -Amn$, where $|m| < m_o$, $|n| < n_o$ and $(m,n) \neq (0,0)$.

This requirement can be satisfied by sequential solution for the compensation part of the reconstruction code Tmn.

(e) In order to obtain this solution, first the corner points of the recording code Smn are defined. The corner points contain the indices $(\mu_1, \nu_1)$ for downwards left, $(\mu_2, \nu_2)$ for downwards right, $(\mu_3, \nu_3)$ for upwards right, and $(\mu u_4, \nu_4)$ for upwards left. Movement to the right means that m increases, whilst upwards movement means that n increases. The matrix element $S\mu_1, \nu_1$ thus represents the point which is situated furthest to the bottom left.

(f) Subsequently, a coupling is required between the characteristic numbers of the matrix Amn and the corner points of the recording code Smn. This coupling is necessary because for a sequential solution for the compensation part of the reconstruction code Tmn matrix elements are chosen from Smn which are dependent on the characteristic numbers of the matrix elements Amn. To this end, an image is defined:

$$(\alpha\ mn, \beta\ mn) = \begin{cases} (\mu_1, \nu_1) \text{ for } m > 0\ n \geq 0 \\ (\mu_2, \nu_2) \text{ for } m \leq 0\ n > 0 \\ (\mu_3, \nu_3) \text{ for } m < 0\ n \leq 0 \\ (\mu_4, \nu_4) \text{ for } m \geq 0\ n < 0 \end{cases} \quad (6)$$

EXAMPLE $m=1, n=2$. Therefrom it follows that: $m > 0, n > 0$, so $(\alpha_{12}, \beta_{12}) = (\mu u_1, \nu_1)$.

(g) Furthermore, the matrix elements Amn must be arranged. In FIG. 10 a sequence of numbers is arranged at points of intersection of a quadratic lattice, starting in the centre (0) and proceeding counter-clockwise. After each revolution, a new start is made at a point with $m \geq 0, n = 0$. This arrangement enables the determination of a separate pair of characteristic numbers (m, n) by a number N, and hence of a matrix element Amn. Example: Assuming that $(m, n) = (2, 1)$, $N = N(m, n) = N(2, 1) = 10$.

Using the arrangement according to FIG. 10, the matrix Amn can be determined by an index N. A $(N) = Amn$.

(h) Finally, the matrix elements Tmn are arranged. Therefore, it is defined that $T(N) = T_{60\ mn-m,\ \beta_{mn}-n}$.

Example:
$(m,n) = (1,2)$. It follows therefrom that $(\alpha_{1,2}, \beta_{1,2}) = (\mu_1, \nu_1)$ and $N = (\mu_1 - 1, \nu_1 - 2)$ and $T(N) = T(\mu_1 1, \nu_1 - 2)$.

(i) The equation to be solved was:

$$Cmn = \sum_{j=-\infty}^{\infty} \sum_{k=-\infty}^{\infty} \overset{*}{S}m+j, n+k\ Tjk = -Amn \quad (7)$$

for $|m| < m_o, |n| < n_o$ and $(m,n) \neq 0$.

(j) A sequential solution is $$T(0) = 0 \quad (8)$$
$$T(N) = -\left[\overset{*}{A}mn + \sum_{0 \leq N' \leq N} \overset{*}{S}m+j, n+k\ T(N')\right] / S^*_{\alpha mn, \beta mn}$$

where $TjK = T(N')$ for $N' < N$.

(k) A two-point distribution as described with reference to the FIGS. 3a–g is used as an example. For the recording code Sm, $S_{1,0} = 1$ and $S_{-1,0} = 1$, otherwise $Smn = 0$. As a result, $A_{0,0} = 2$, $A_{2,0} = 1$, $A_{-2,0} = 1$ (formule 1). $0 < N \leq 24$ (see FIG. 10) is found for an artefact-free area with $-3 < m < 3, -3 < n < 3$. The corner points of the matrix Smn are $$(\mu_1, \nu_1) = (-1, 0) \quad (9)$$
$$(\mu_2, \nu_2) = (1, 0)$$
$$(\mu_3, \nu_3) = (1, 0)$$
$$(\mu_4, \nu_4) = (-1, 0).$$

The solution of the formula (8) can be determined as shown in the following table:

| N | (m,n) | (α,β) | (α−m, β−n) | T(N) |
|---|---|---|---|---|
| 0 | | | | T(0) = 0 |
| 1 | (1,0) | (−1,0) | (−2,0) | $T(1) = -(A^*_{1,0} + 0)/S^*_{-1,0} = 0$ |
| 2 | (1,1) | (−1,0) | (−2,−1) | T(2) = 0 |
| 3 | (0,1) | (1,0) | (1,−1) | T(3) = 0 |
| 4 | (−1,1) | (1,0) | (2,−1) | T(4) = 0 |
| 5 | (−1,0) | (1,0) | | T(5) = 0 |
| 6 | (−1,−1) | (1,0) | | T(6) = 0 |
| 7 | (0,−1) | (−1,0) | | T(7) = 0 |
| 8 | (1,−1) | (−1,0) | | T(8) = 0 |
| 9 | (2,0) | (−1,0) | (−3,0) | $T(9) = -(A^*_{2,0} + 0)/S^*_{-1,0}$ <br> $= -1 = T_{-3,0}$ |
| 10 | (2,1) | (−1,0) | (−3,−1) | $T(10) = -(A^*_{2,1} + T_{-3,0}S^*_{-1,1})/S^*_{-1,0} = 0$ |
| 11 | (2,2) | (−1,0) | | T(11) = 0 |
| 12 | (1,2) | (−1,0) | | |
| 13 | (0,2) | (1,0) | | |
| 14 | (1−,2) | (1,0) | | |
| 15 | (−2,2) | (1,0) | | |
| 16 | (−2,1) | (1,0) | | |
| 17 | (−2,0) | (1,0) | (3,0) | $T(17) = -(A^*_{-2,0} + T_{-3,0}S_{-5,0}/S^*_{1,0} =$ <br> $-1 = T_{3,0}$ |
| T(18) to T(48) = 0 | | | | |
| 49 | (4,0) | (−1,0) | (−5,0) | $T(49) = -(A^*_{4,0} + T_{-3,0}S^*_{+1,0} + T_{3,0}$ |

|                |        |       |       | -continued                                           |
|----------------|--------|-------|-------|------------------------------------------------------|
|                |        |       |       | $S^*_{1,0}/S^*_{-1,0} =$                             |
| T(50) to T(64) | = 0    |       |       |                                                      |
| 65             | (−4,0) | (1,0) | (5,0) | $T(65) = -(A^*_{-4,0} + T_{-3,0}S^*_{-7,0} + T_{3,0}$ |
|                |        |       |       | $S^*_{-1,0} + T_{-5,0}S^*_{-9,0})/S^*_{1,0}$         |
|                |        |       |       | $= +1 = T_{5,0}$                                     |

The values $(\alpha, \beta)$ and $(\alpha mn, \beta mn)$ are obtained from the formule (6) in combination with the formule (9). For predetermined (m, n), the formule (6) is used to find the associated $(\mu\nu)$ with which the values in the formule (9) are associated.

The compensation code is then $$Kmn = Smn + Tmn$$

Therefore, for this example:

$K_{1,0} = 1$ ⎫ Predetermined by Smn, because the compensation code Kmn contains the
$K_{-1,0} = 1$ ⎭ recording code Smn.

$K_{-3,0} = -1$  determined from Tmn $K_{3,0} = -1$ ⎫
$K_{-5,0} = 1$ ⎬ determined from Tmn
$K_{5,0} = 1$ ⎭

This compensation code Kmn is shown in FIG. 3g as the compensating code K'. For other recording distributions, for example, the threepoint distribution of FIG. 4a or distributions comprising more points (for example, 24 points), compensation codes Kmn can be determined in a similar manner.

The solution steps are always:

(1) Selection of a recording distribution Smn and conversion into the form of a matrix.

(2) Determination and indication of the corner points of the recording distribution Smn.

(3) Successive application of the solution formule (8) with the aid of FIG. 10.

During the calculation of T(N)

(a) $\alpha_{mn}$, $\beta_{mn}$ and $\alpha_{mn} - m$, $\beta_{mn} - n$ are determined, and (b) $(m+j, n+k)$ are calculated for all $(j,k)$, where $TjK = T(N')$ for $N' < N$.

The FIGS. 6 to 9 show various devices for obtaining planigrams which are artefact-poor at least in their centre by means of the method in accordance with the invention.

In FIG. 6, a light box 30 irradiates a superposition image 31, for example, with white light. A lens matrix 32 wherethrough an optical system axis 33 extends perpendicularly produces a real three-dimensional image 34 in the superposition zone 35. Using a ground glass plate 36, which can be displaced at random within the image 34, a relevant slice of the object is imaged for example, an oblique slice. The ground glass plate 36 may furthermore be connected to a Fresnel lens 63a which acts as a field lens in order to increase the brightness of the layer image.

The individual lenses of the lens matrix, being arranged in accordance with the point distribution of the compensation code, for example, the code K" of FIG. 4i, are covered by different colour filters 32a, b. For example, the lenses arranged at the points of the code K" having the amplitude −1 are covered by red filters, whilst the lenses which are arranged at the points of the code K" having the amplitude −1 are covered by blue filters. A beam splitter 38 which is displaceable in the direction of the optical axis 33 and which is arranged behind the ground glass plate 36 splits the light into two beams, one of which extends parallel whilst the other extends perpendicularly to the optical axis 33. Using two objectives 39 and 40, the image of the ground glass plate is each time projected on a television camera 41, 42, one camera comprising a red filter 43 as an input filter, whilst the other camera comprises a blue filter 44 as the input filter.

Thus, the camera 41 receives only red radiation, whilst the camera 42 receives only blue radiation. By synchronous scanning of the two images and by subtraction of the video output signals of the two cameras 41 and 42 by means of a subtractor 45, layer images can be made which are artefact-poor at least in their centre and which can be displayed, for example, on a monitor 46.

FIGS. 7 and 8 each time show a two-channel construction. On two optical axes 47 and 48 which extend parallel with respect to each other two light boxes 30 are arranged, superposition images 31 and negative superposition images 31a being present in front of each box. A lens matrix 49 in this case only comprises the lenses which are arranged at points of positive amplitude −1 of a compensating code, for example, the code K". A second lens matrix 50 only comprises the lenses which are situated at points of negative amplitude −1.

In FIG. 7, the images obtained by means of the arbitrarily but synchronously movable ground glass plate 36 are projected, via Fresnel lenses 36a which act as field lenses and which are rigidly connected to the ground glass plates 36, and via objectives 51 and 52, each time on a television camera 53, 54. The image synchronized output signals of the two cameras 51 and 52 are then added in an adder 55 in order to obtain artefact-free layer images which are displayed on a monitor 56.

In FIG. 8, the images obtained by means of the ground glass plates 36 are projected onto a television camera 60 by means of a flat mirror 57 and a semitransparent plate 58 which are displaceable in the direction of the optical axis 47 and 48, respectively, via a separate objective 59, said television camera being connected to a monitor 61 for a display and to a memory 62 for the storage of the layer images.

FIG. 9 shows a holographic construction for performing the method in accordance with the invention. On an optical axis 63 there is situated a lens 64 which converts a parallel, monochromatic radiation beam 65 into a converging radiation beams. At the point of convergence there is present a Fourier hologram H in which the Fourier transform of a compensating code is present, for example, that of the code K". Between the hologram H and the lens 64 there is present the superposition image 31 which is projected, via a second lens 66 which is situated behind the hologram H, in an image plane 67. The superposition image 31, the lens 66 and the image plane 67 are mechanically interconnected via a system of rods 68 and can be displaced parallel with respect to the optical axis 63 (arrow 69) for the display of different layer images.

The hologram H can be produced by means of a hole diaphragm which is irradiated from the rear by means of coherent light and a reference beam, the distribution of the holes in the hole diaphragm corresponding to the distribution of the points of a compensating code (or the distribution of the imaging elements). During the recording of the hologram, the holes which generate the imaging elements whereby correction perspective images are superposed on the artefact images, are covered by transparent plates for the formation of a phase difference amounting to an odd multiple of half the wavelength $\lambda$ of the coherent light. Therefore, the thickness d of the plates is $(\lambda/2) \cdot n$, where $n=1, 3, 5, \ldots$. The imaging elements generated by the covered holes in the hologram then correspond to imaging elements, for example, lenses, which are arranged at the points of negative amplitude of a compensating code, for example, of the code K" in FIG. 4i.

Obviously, the hologram H can also be obtained by means of a computer which calculates the hologram from a predetermined compensating code.

What is claimed is:

1. Apparatus for decoding a recording of a coded superposition image which is composed of a large number of separate primary perspective images of an object and was formed by irradiating the object with radiation from a pluarlity of radiation sources which were distributed in a geometric configuration in a plane comprising:
    a white light source disposed to irradiate the recording;
    a lens matrix, disposed parallel to the recording, for transmitting light received from the recording, the lens matrix including primary lenses which are distributed in the matrix in a geometric configuration which corresponds to the configuration of the radiation sources and correction lenses which are distributed in the matrix to produce compensating images over artefact images produced by the primary lenses;
    first color filters disposed to filter light transmitted through each of the primary lenses;
    second color filters, having light transmission characteristics which differ from the first color filters, disposed to filter light transmitted through each of the correction lenses;
    beam splitter means disposed to receive light from the recording which is transmitted through the lens matrix for splitting that light into a first beam and a second beam;
    a first input filter, having the same light transmission characteristics as the first color filters, disposed to filter the first beam;
    a second input filter, having the same light transmission characteristics as the second color filters, disposed to filter the second beam;
    first image pick-up tube means for receiving the filtered first beam and producing a first electrical signal corresponding thereto;
    second image pick-up tube means for receiving the filtered second beam and producing a second electrical signal corresponding thereto; and
    subtractor means for subtracting the second electrical signal from the first electrical signal to produce an output electrical signal which corresponds to a corrected decoded image.

2. In an apparatus for decoding a recording of a coded superposition image which was formed by irradiating an object with radiation from a plurality of radiation sources distributed in a geometric configuration in a plane and recording the superposed separate primary perspective images thus produced, of the type which comprises: p1 a light source disposed to illuminate the recording; a matrix of a like plurality of primary imaging elements which are disposed in a plane in a geometric configuration which corresponds to the configuration of the radiation sources; and image detecting means for recording and/or visualizing a primary decoded image formed by light which is transmitted from the recording, through the matrix; the improvement, for reducing artefacts produced by the primary imaging elements, in at least a central portion of the decoded image, which comprises:
    an additional matrix of compensating imaging elements for projecting a correction perspective image derived from the recording onto each artefact in at least in the central portion of the decoded image, whereby those artefacts are at least partially cancelled.

3. The apparatus of claim 2 wherein the means for recording and/or visualizing comprise first television pick-up tube means for receiving the primary image and producing a first electrical signal corresponding thereto; second television pick-up tube means for receiving the correction image and producing a second electrical signal corresponding thereto and means for combining the first electrical signal and the second electrical signal to produce an output electrical signal corresponding to the compensated decoded image.

4. The apparatus of claim 3 wherein the matrix of primary elements and the additional matrix are disposed in a plane in a common optical path and further comprising:
    first color filters disposed to filter light transmitted by the primary imaging elements and light received by the first television pick-up means;
    second color filters, which have light transmission characteristics which differ from those of the first color filters, disposed to filter light transmitted by the compensating image element means and light received by the second television pick-up means; and
    means for splitting light transmitted through the primary imaging elements and second imaging elements into two separate beams and projecting those beams, respectively, for reception by the first and second television pick-up means.

5. The apparatus of claim 3 wherein the matrix of primary elements and the first pick-up tube means are disposed on a first optical path and the additional matrix and second pick-up tube means are disposed on a second, separate optical path.

6. The apparatus of claim 2, 3, or 4 wherein the imaging elements comprise lenses.

7. The apparatus of claim 2 or 3 wherein the imaging elenents comprise one or more holograms.

8. In a method for making planigrams of a three-dimensional object which comprises the steps of:
    irradiating the object with radiation from a plurality of radiation sources, which are configured in a plane, to form a coded superposition image which is composed of a like plurality of separate primary perspective images;
    making a recording of the superposition image; and
    subsequently decoding the superposition image by imaging the recording through a matrix which comprises a like plurality of imaging elements, which are distributed in a geometric configuration which corresponds to the configuration of the radiation sources, to form a decoded image; the improvement comprising the steps of:

further imaging the recording through an additional matrix of imaging elements to form correction perspective images over at least some artefacts in the decoded image and subtracting the correction perspective images from the decoded image to compensate for the artefacts, at least in the center of the decoded image.

9. The method of claim 8 further comprising the steps of detecting the decoded image and the correction images on one or more television pick-up tubes to produce corresponding output signals and wherein the subtracting step comprises subtracting one of the output signals from another.

10. The method of claim 8 or 9 wherein the recorded superposition image is imaged by illuminating it with white light and further comprising the steps of filtering the light transmitted through the primary imaging elements with a first color filter and filtering the light transmitted through the correction imaging elements with a second color filter.

11. The method of claim 10 wherein two pickup tubes are utilized in the decoding step and further comprising the step of filtering light detected by pickup tubes with filters which correspond to the first and second filters respectively.

* * * * *